(12) United States Patent
Campbell et al.

(10) Patent No.: US 10,072,120 B2
(45) Date of Patent: Sep. 11, 2018

(54) FUNCTIONALIZED POLYHYDROXYALKANOATE MATERIALS FORMED FROM AN UNSATURATED POLYHYDROXYALKANOATE MATERIAL

(71) Applicant: International Business Machines Corporation, Armonk, NY (US)

(72) Inventors: Eric J. Campbell, Rochester, MN (US); Sarah K. Czaplewski, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/367,826

(22) Filed: Dec. 2, 2016

(65) Prior Publication Data

US 2018/0155495 A1    Jun. 7, 2018

(51) Int. Cl.
*C12P 7/62* (2006.01)
*C12P 11/00* (2006.01)
(Continued)

(52) U.S. Cl.
CPC ............ *C08G 63/912* (2013.01); *C12P 7/625* (2013.01)

(58) Field of Classification Search
CPC .......... C08L 67/04; C08L 67/02; C08L 61/22; C08L 79/04; C08L 21/00; C08L 2666/02; C08L 2666/34; C08L 2666/54; C08L 101/12; C08L 23/10; C12P 7/625; C12P 11/00; C12N 9/0006; C12N 9/1029; C12N 9/93
See application file for complete search history.

(56) References Cited

U.S. PATENT DOCUMENTS

| 5,395,919 | A | 3/1995 | Lee et al. |
| 6,495,152 | B2 | 12/2002 | Steinbuchel et al. |

(Continued)

FOREIGN PATENT DOCUMENTS

| WO | WO-1989/000202 A2 | 1/1989 |
| WO | WO-1995/020621 A1 | 8/1995 |

OTHER PUBLICATIONS

A.Steinbuchel "Diversity of bacterial polyhydroxyalkanoic acids" 1995,pp. 219-229.*

(Continued)

*Primary Examiner* — Ling Choi
*Assistant Examiner* — Gennadiy Mesh
(74) *Attorney, Agent, or Firm* — Roy R. Salvagio; Robert R. Williams; Kennedy Lenart Spraggins LLP

(57) ABSTRACT

A process of forming a functionalized polyhydroxyalkanoate (PHA) material includes performing an oxide elimination reaction (e.g., a selenoxide elimination reaction or a sulfoxide elimination reaction) on a saturated PHA material to form an unsaturated PHA material having a carbon-carbon double bond in a polymer backbone. The process also includes utilizing the unsaturated PHA material to form a functionalized PHA material. The functionalized PHA material has one or more cross-linkable functional groups (e.g., one or more thiol groups) bonded to a polymer backbone of the functionalized PHA material.

6 Claims, 10 Drawing Sheets

Saturated PHA Material (e.g., P4HB) → Oxide elimination reaction (e.g., selenoxide elimination reaction) → Unsaturated PHA Material with carbon-carbon double bond in PHA backbone

(51) Int. Cl.
*C08G 63/91* (2006.01)
*C08L 67/04* (2006.01)

(56) References Cited

U.S. PATENT DOCUMENTS

| | | | |
|---|---|---|---|
| 6,821,612 | B1 | 11/2004 | Melik et al. |
| 6,828,357 | B1 | 12/2004 | Martin et al. |
| 6,908,720 | B2 | 6/2005 | Kenmoku et al. |
| 8,168,550 | B2 | 5/2012 | Collias et al. |
| 8,771,720 | B2 | 7/2014 | Williams et al. |
| 9,023,972 | B2 | 5/2015 | Chu et al. |
| 9,474,830 | B2 | 10/2016 | Seliktar et al. |
| 9,475,930 | B2 | 10/2016 | Weinlein et al. |
| 2002/0028857 | A1 | 3/2002 | Holy |
| 2006/0147412 | A1* | 7/2006 | Hossainy ............ C08B 37/0072 424/78.27 |
| 2015/0290344 | A1 | 10/2015 | Alexis et al. |

OTHER PUBLICATIONS

Fer et al. "An Effi cient Thiol-Ene Chemistry for the Preparation of Amphiphilic PHA-Based Graft", Macromol, 2012.*
Gomez et al., "Figure 1", from, "Chapter 3: Making Green Polymers Even Greener: Towards Sustainable Production of Polyhydroxyalkanoates from Agroindustrial By-Products", of, "Advances in Applied Biotechnology", Edited by Marian Petre, Jan. 2012, p. 43, InTechOpen.com (online), URL: intechopen.com/books/advances-in-applied-biotechnology/making-green-polymers-even-greener-towards-sustainable-production-of-polyhydroxyalkanoates-from-agro.
Roy et al., "Modification of Polyhydroxyalkanoates (PHAs)", Chapter 7 of, "Polyhydroxyalkanoate (PHA) based Blends, Composites and Nanocomposites", Nov. 2014, pp. 149-150, Royal Society of Chemistry, London, UK.
Reich, "Sulfoxide and Selenoxide syn-Eliminations", Advanced Organic Chemistry Course, Fall 2013, 5 pages, University of Wisconsin, Madison, [accessed Sep. 7, 2016], URL: www.chem.wisc.edu/areas/reich/chem547/2-redox%7B19%7D.htm.
Lakshmi et al., "Reactivity Studies of Maleimide Epoxy Resin With Long Chained Amines", Journal of the Chilean Chemical Society, vol. 56, No. 3, 2011, pp. 725-728, Scientific Electronic Library Online (SciELO) Chile, URL: http://www.scielo.cl/scielo.php?pid=S0717-97072011000300001&script=sci_arttext.
DuPont, "DuPont Industrial Biosciences and ADM Announce Breakthrough Platform Technology for Long Sought-After Molecule", Jan. 2016, 7 pages, DuPont.com (online), Wilmington, DE, URL: www.dupont.com/products-and-services/industrial-biotechnology/press-releases/dupont-adm-announce-platform-technology-for-long-sought-after-molecule.html.

\* cited by examiner

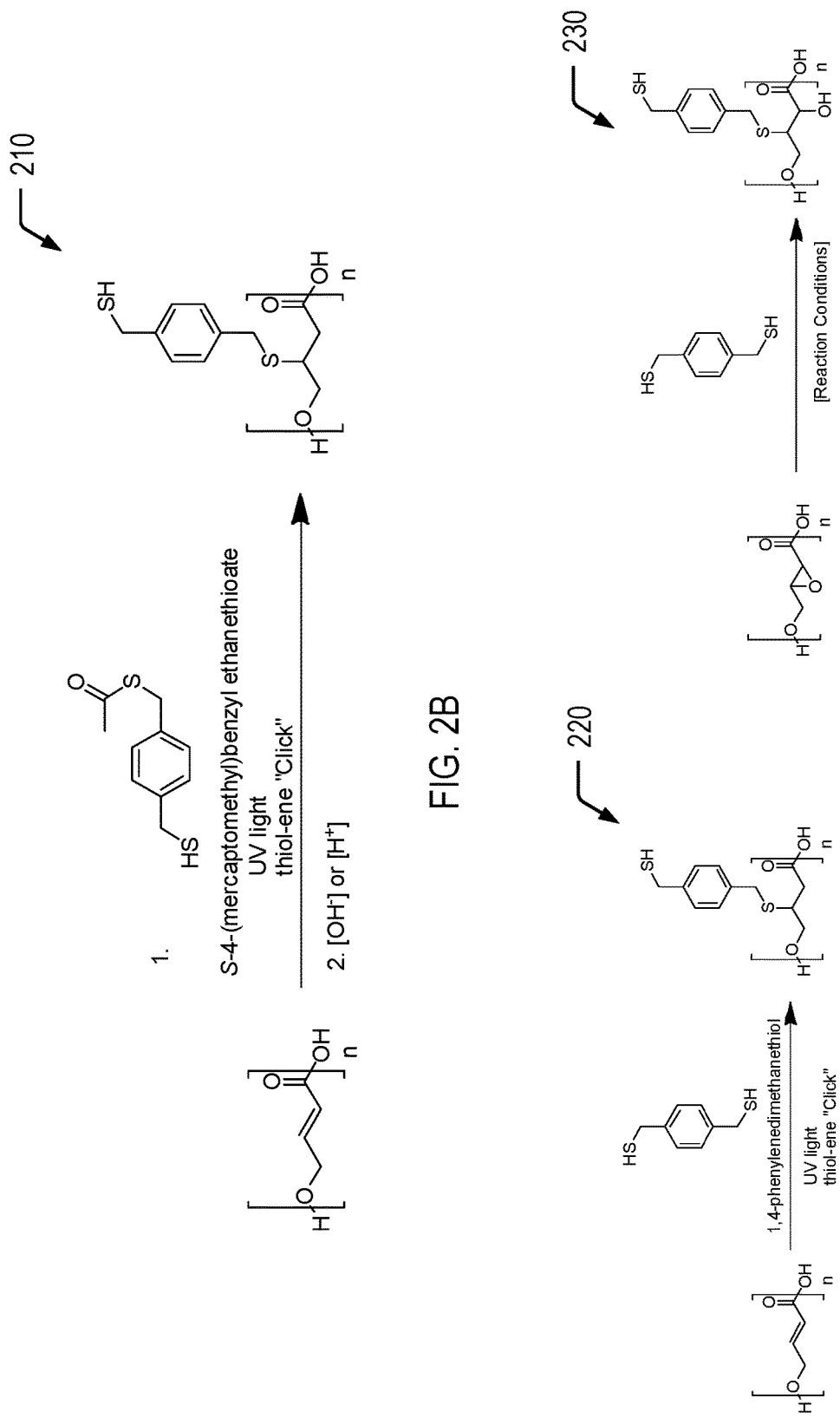

FUNCTIONALIZED POLYHYDROXYALKANOATE MATERIALS FORMED FROM AN UNSATURATED POLYHYDROXYALKANOATE MATERIAL

BACKGROUND

Plastics are typically derived from a finite and dwindling supply of petrochemicals, resulting in price fluctuations and supply chain instability. Replacing non-renewable petroleum-based polymers with polymers derived from renewable resources may be desirable. However, there may be limited alternatives to petroleum-based polymers in certain contexts. To illustrate, particular plastics performance standards may be specified by a standards body or by a regulatory agency. In some cases, alternatives to petroleum-based polymers may be limited as a result of challenges associated with satisfying particular plastics performance standards.

SUMMARY

According to an embodiment, a process of forming a functionalized polyhydroxyalkanoate (PHA) material is disclosed. The process includes forming an unsaturated PHA material having a carbon-carbon double bond in a polymer backbone. The process also includes utilizing the unsaturated PHA material to form a functionalized PHA material. The functionalized PHA material has one or more cross-linkable functional groups bonded to a polymer backbone of the functionalized PHA material.

According to another embodiment, a process of forming a functionalized PHA material is disclosed. The process includes forming a saturated PHA material via a bacterial fermentation process. The process includes performing an oxide elimination reaction on the saturated PHA material to form an unsaturated PHA material having a carbon-carbon double bond in a polymer backbone. The process also includes forming an epoxidized PHA material from the unsaturated PHA material. The process further includes utilizing the epoxidized PHA material to form a functionalized PHA material. The functionalized PHA material has one or more cross-linkable functional groups bonded to a polymer backbone of the functionalized PHA material.

According to another embodiment, a process of forming a reversibly cross-linked PHA material is disclosed. The process includes forming a functionalized PHA material from an unsaturated PHA material having a carbon-carbon double bond in a polymer backbone. The functionalized PHA material has one or more cross-linkable functional groups bonded to a polymer backbone of the functionalized PHA material. The process also includes initiating a reversible chemical reaction between a first cross-linkable functional group of a first functionalized PHA material and a second cross-linkable functional group of a second functionalized PHA material to form a reversibly cross-linked PHA material.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

BRIEF DESCRIPTION OF THE DRAWINGS

FIGS. 2B-2D are chemical reaction diagrams illustrating alternative embodiments of processes of forming a functionalized PHA material containing thiol group(s) bonded to a PHA backbone.

DETAILED DESCRIPTION

The present disclosure describes functionalized PHA materials and methods of forming functionalized PHA materials from an unsaturated PHA material. The unsaturated PHA material has a carbon-carbon double bond in a PHA backbone. After forming the carbon-carbon double bond in the PHA backbone, the unsaturated PHA material may be utilized to form a functionalized PHA material having one or more functional groups bonded to the polymer backbone of the functionalized PHA material. The one or more functional groups may enable cross-linking and/or reversibly bonding of a polymer backbone of one functionalized PHA material to a polymer backbone of another functionalized PHA material.

PHA materials are a group of storage polymers produced by many types of bacteria in response to growth restriction by a nutrient other than the carbon source. To illustrate, *Pseudomonas oleovorans* is an example of a microorganism that produces PHAs. Other suitable bacteria may be utilized in other cases.

In contrast to PHA modification techniques where long alkyl chains extend from the polymer backbone, forming the carbon-carbon double bond in the PHA backbone prior to functionalization enables a variety of functional groups to be added closer to the PHA backbone. Bonding the functional groups closer to the PHA backbone results in a more rigid structure than PHA materials with long alkyl chains extending from the PHA backbone. By not having the side chain(s) present in the polymer (that influence materials properties) before modification may enable one of ordinary skill in the art to selectively modify some of the backbone of the polymer.

The mechanical properties of the polymer can be tuned by varying the chain length of the aliphatic fatty acid(s) used in forming the PHAs or by varying the length of the PHAs themselves, which may be achieved by modifying reaction conditions, such as time, temperature, and the bacteria chosen for fermentation. In some cases, the PHA materials of the present disclosure may be utilized as stand-alone polymers or may be blended with other plastics (e.g., those derived from non-renewable sources) for varying applications. Illustrative examples of plastics for blending include polylactic acid, polyurethanes, polycarbonates, acrylonitrile butadiene styrene (ABS), polyesters, polyethers, or combinations thereof, among other alternatives. The appropriate blend ratio may vary in order to achieve a desired combination of mechanical properties.

Figure 1:
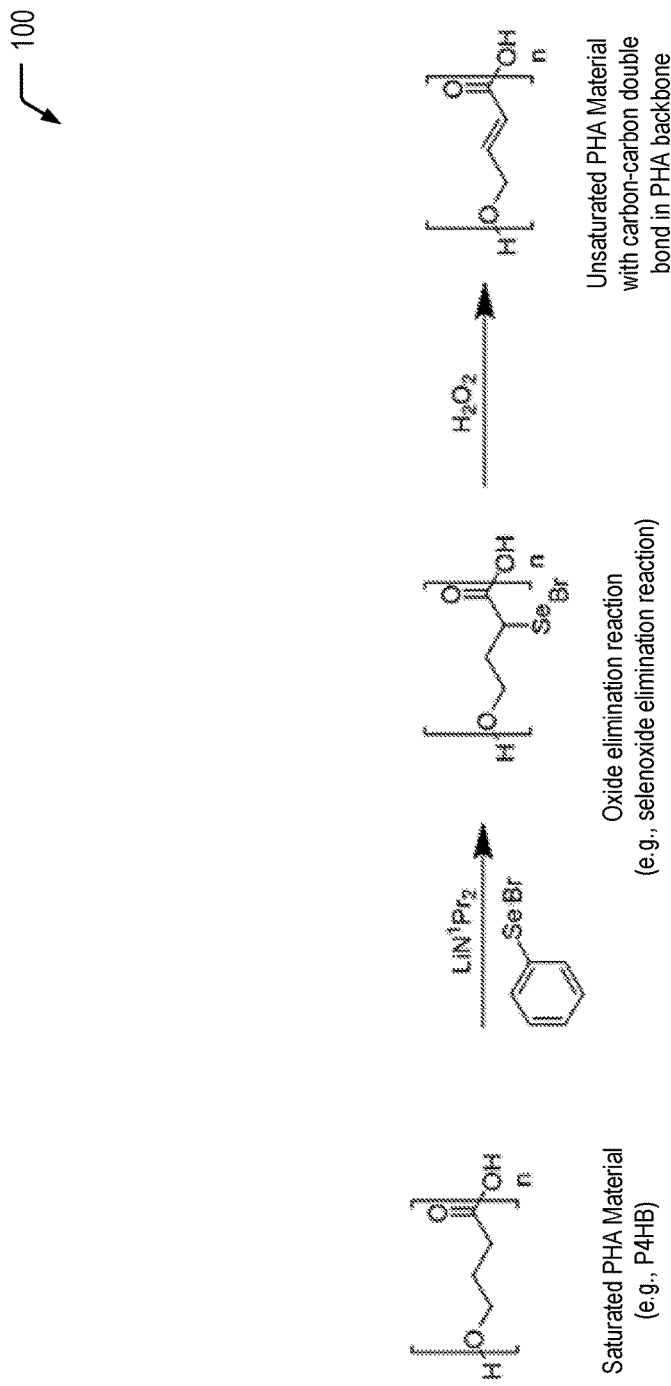
FIG. 1 is a chemical reaction diagram illustrating a process of forming an unsaturated PHA material having a carbon-carbon double bond in a polymer backbone, according to one embodiment.

Referring to FIG. 1, a chemical reaction diagram 100 illustrates an example of a process of forming an unsaturated PHA material having a carbon-carbon double bond in a polymer backbone, according to one embodiment. As described further herein, the unsaturated PHA material depicted in FIG. 1 may be utilized to form various functionalized PHA materials having one or more cross-linkable functional groups bonded to a polymer backbone of the functionalized PHA material. As illustrated and further described herein with respect to FIGS. 2A-2D, 4, 6 and 7, the functional group(s) may include thiol group(s), a coumarin group, a diene group, or a dienophile group (among other alternative moieties or combinations of moieties). As illustrated and further described herein with respect to FIGS. 3, 5, and 8, the functional group(s) enable the formation of a reversibly cross-linked PHA material via a reversible chemical reaction, including a disulfide formation reaction, a coumarin photodimerization reaction, or a Diels-Alder reaction.

In the example of FIG. 1, the unsaturated PHA material having the carbon-carbon double bond in the PHA backbone is synthesized from a saturated polymeric material that may be produced via a bacterial fermentation process of monomer material(s). While not shown in the example of FIG. 1, in alternative embodiments, the carbon-carbon double bond may be formed prior to the bacterial fermentation process. Thus, in some cases, forming the unsaturated PHA material depicted on the right side of the chemical reaction diagram of FIG. 1 may include forming an unsaturated monomer material and subsequently performing the bacterial fermentation process to polymerize the unsaturated monomer material, with the carbon-carbon double bond maintained during the bacterial fermentation process.

In the particular embodiment depicted in FIG. 1, the saturated PHA material illustrated on the left side of the chemical reaction diagram includes poly-4-hydroxybutyrate (P4HB). Other examples of saturated PHA materials that may be utilized include poly-3-hydroxybutyrate (P3HB) or poly(3-hydroxybutyrate-co-3-hydroxyvalerate) (PHBV), among other alternatives. One potential advantage associated with the selection of P4HB as the saturated PHA material is that it includes a backbone that is sufficiently long for an oxide elimination reaction to form the carbon-carbon double bond in the PHA backbone. Another potential advantage associated with the selection of P4HB as the saturated PHA material is that P4HB does not include dangling side chains extending from the PHA backbone.

FIG. 1 illustrates that an oxide elimination reaction may be performed on the saturated PHA material. In the particular embodiment depicted in FIG. 1, the oxide elimination reaction is a selenoxide elimination reaction. In an alternative embodiment (not shown in FIG. 1), a sulfoxide elimination process may be utilized to form the PHA material having the carbon-carbon double bond in the polymer backbone. Alternatively, a bromide elimination may also be utilized. Such a bromide elimination reaction involves a radical bromination alpha to the carbonyl group (bromine or N-bromosuccinimide with UV light or heat and radical initiator, such as benzoyl peroxide or AIBN), followed by an elimination of the bromine with a hindered amine base such as triethylamine or DBU. FIG. 1 illustrates that the selenoxide elimination reaction results in the formation of the unsaturated PHA material having the carbon-carbon double bond in the PHA backbone. Forming the carbon-carbon double bond in the PHA backbone prior to functionalization enables a variety of functional groups to be added closer to the PHA backbone. Bonding the functional groups closer to the PHA backbone results in a more rigid structure than PHA materials with long alkyl chains extending from the PHA backbone.

Prophetic Example: Formation of unsaturated PHA material having a carbon-carbon double bond in a PHA backbone. To a solution of PHA (1.0 eq.) in THF at −78° C., under argon, LDA (2 M solution, 1.1 eq.) may be added. The mixture may be stirred at −78° C. for 30 minutes and may be gradually warmed to 0° C. or ambient temperature. To this mixture may be added a PhSeCl or PhSeBr (1.05 eq.) solution in THF at −78° C. The reaction mixture may be stirred at −78° C. or 0° C. or at ambient temperature for another 30 min, and may be subsequently warmed up to room temperature. Any resulting solids may be filtered off. The solvents may be removed in vacuo or the polymer may be precipitated into a cold, organic non-solvent such as methanol, acetone, or hexane and may be filtered. The crude polymer may be dissolved in dichloromethane, to which may be added diisopropylamine (2.0 eq.) followed by m-CPBA (1.1 eq.). The mixture may be stirred at 0° C. for 30 min, then warmed to refluxing for 6 hours. The polymer may be precipitated into a cold, organic non-solvent such as methanol, acetone, or hexane and may be filtered. The polymer may be purified by any combination of Soxhlet extraction, reprecipitation, filtration, column chromatography, or other techniques.

Thus, FIG. 1 illustrates an example of a process of forming an unsaturated PHA material having a carbon-carbon double bond in a PHA backbone. As further described herein, the carbon-carbon double bond in the PHA backbone may be utilized to bond one or more functional groups to the PHA backbone. The functional group(s) that are bonded to the PHA backbone may be utilized to form a reversibly cross-linked PHA material via a reversible chemical reaction, including a disulfide formation reaction, a coumarin photodimerization reaction, or a Diels-Alder reaction.

Figure 2A:
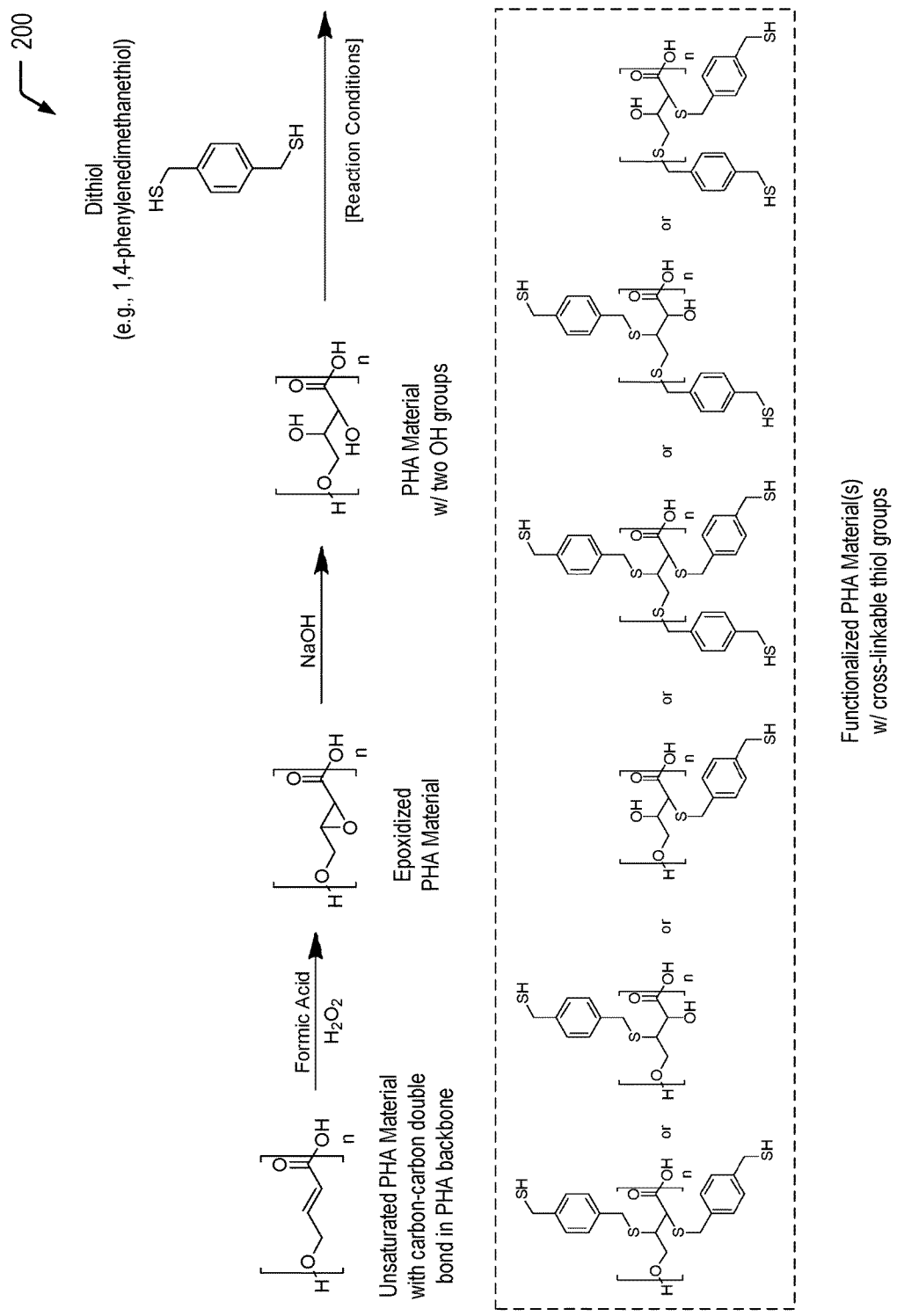
FIG. 2A is a chemical reaction diagram illustrating a process of utilizing the unsaturated PHA material depicted in FIG. 1 to form a functionalized PHA material containing thiol group(s) bonded to a PHA backbone, according to one embodiment.

Referring to FIG. 2A, a chemical reaction diagram 200 illustrates an example of a process of utilizing the unsaturated PHA material having the carbon-carbon double bond in the PHA backbone that is depicted in FIG. 1 to form a functionalized PHA material containing cross-linkable thiol group(s) bonded to the PHA backbone, according to one embodiment. As illustrated and further described herein with respect to FIG. 3, one or more of the thiol group(s) may be utilized to form disulfide linkage(s) to reversibly cross-link a polymer backbone of one PHA material to a polymer backbone of another PHA material.

The first chemical reaction depicted in FIG. 2A illustrates that the carbon-carbon double bond in the PHA backbone of the unsaturated PHA material of FIG. 1 may be utilized to form an epoxidized PHA material having an epoxide group in the PHA backbone. The second chemical reaction depicted in FIG. 2A illustrates that an epoxide ring-opening reaction may be performed on the epoxidized PHA material to form an intermediate material that includes two hydroxyl groups. FIG. 2A further illustrates that the intermediate material may be chemically reacted with a dithiol to form one or more functionalized PHA materials with one or more thiol groups bonded to a polymer backbone of the functionalized PHA material(s). In the particular embodiment depicted in FIG. 2A, the dithiol includes 1,4-phenylenedimethanethiol. In other cases, alternative and/or additional dithiol materials may be utilized. As illustrated and described further herein with respect to FIG. 3, the thiol groups bonded to the polymer backbone of the functionalized PHA material(s) of FIG. 2A may represent locations for (reversible) cross-linking via one or more disulfide formation reactions.

In a particular embodiment, the epoxidized PHA material may be formed from the unsaturated PHA material of FIG. 1 using formic acid and hydrogen peroxide. In a particular embodiment, saponification conditions (e.g., NaOH) may be utilized to form the PHA material with the two hydroxyl groups from the epoxidized PHA material.

FIG. 2A illustrates six examples of functionalized PHA materials that may be formed via the chemical reaction with the dithiol. From left to right, the first functionalized PHA material of FIG. 2A includes two thiol groups are bonded to the PHA backbone. The second and third functionalized PHA materials of FIG. 2A include one thiol group bonded to the PHA backbone without a terminal thiol group. The fourth functionalized PHA material of FIG. 2A includes two thiol groups bonded to the PHA backbone and a terminal thiol group. The fifth and sixth functionalized PHA materials of FIG. 2A include one thiol group bonded to the PHA backbone and a terminal thiol group.

As a prophetic example, the reaction may require a catalyst system of Palladium, (SP-4-2)-dichloro[1,1'-[[(4R, 5R)-2,2-dimethyl-1,3-dioxolane-4,5-diyl]bis(methylene)]bis[1,1-diphenylphosphine-κP]] and silver triflate, in methyl nitrate at 50° C. for 24 hours. The reaction conditions may utilize NaOH in DMF. In some cases, the reaction may have more than one methylene (CH2) groups between the thiol (or protected thiol or halide etc.). To illustrate, in addition to methanethiol, other examples include ethanethiol or propanethiol, among other alternatives. An alternative example of prophetic reaction conditions may include using 4-(chloroalkyl)-benzenemethanethiol, and SN2 conditions (base/polar aprotic solvent). Another alternative example of prophetic reaction conditions may include the use of 4-(mercaptoalkyl)benzoyl chloride, and an amine (pyridine, triethyl amine, etc.).

Thus, FIG. 2A illustrates an example of a process of utilizing the unsaturated PHA material depicted in FIG. 1 to form a functionalized PHA material containing cross-linkable thiol group(s) bonded to a PHA backbone. As further described herein, the thiol group(s) depicted in FIG. 2A may be utilized to form a PHA material that is reversibly cross-linked via disulfide linkage(s). FIGS. 2B, 2C, and 2D depict alternative examples of processes of forming a functionalized PHA material containing a cross-linkable thiol group bonded to the PHA backbone.

Referring to FIG. 2B, a chemical reaction diagram 210 illustrates that, in some cases, a mono-protected thiol may be utilized (e.g., using a thioacetate, such as ethanethionic acid, S-[[4-(mercaptomethyl)phenyl]methyl] ester without a subsequent deprotection step. The reaction should only include the hydroxyl groups, not the carboxylic acid terminal group. As a prophetic example, the reaction may require a sulfonyl chloride and make use of Zn/acetic acid reagents in ethyl acetate, followed by the addition of dichloromethylsilane.

Referring to FIG. 2C, a chemical reaction diagram 220 illustrates an alternative example in which the thiol group(s) may be added to the unsaturated PHA material directly via a thiol-ene "Click" reaction, removing the epoxidation step. As previously described herein with respect to FIG. 2B, the same mono-functionalized or mono-protected thiol reagents/rules may be appropriate. The thiol-ene reaction may utilize UV light and/or heat.

Referring to FIG. 2D, a chemical reaction diagram 230 illustrates an alternative example in which the thiol group(s) may be added directly to the epoxidized PHA material via a nucleophilic ring-opening reaction. As previously described herein with respect to FIG. 2A, the same mono-functionalized or mono-protected thiol reagents/rules may be appropriate. A prophetic example of reaction conditions includes using a Lewis acid, such as scandium(III) triflate or titanium (IV) isopropoxide (e.g., in THF). Each may utilize a base such as sodium ethoxide or sodium hydroxide to deprotonate the thiol first.

Figure 3:
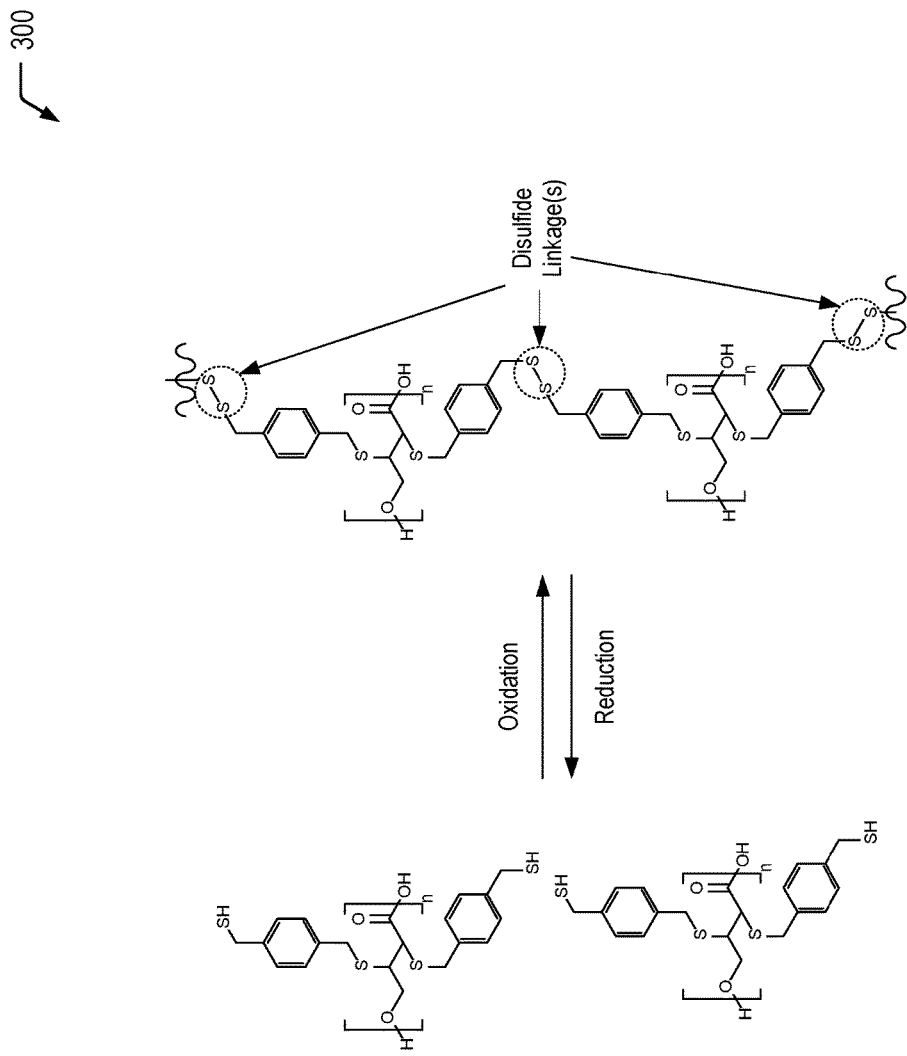
FIG. 3 is a chemical reaction diagram illustrating a process of utilizing one of the functionalized PHA materials depicted in FIG. 2A to form a reversibly cross-linked PHA material, according to one embodiment.

Referring to FIG. 3, a chemical reaction diagram 300 illustrates an example of a process of utilizing one of the functionalized PHA materials depicted in FIG. 2A to form a reversibly cross-linked PHA material. FIG. 3 illustrates that one or more of the thiol group(s) of the functionalized PHA material(s) illustrated in FIG. 2A may chemically react to form disulfide group(s) that may reversibly cross-link the PHA backbones of the functionalized PHA material(s). For illustrative purposes only, the first example functionalized PHA material depicted at the left of FIG. 2A (including two thiol groups bonded to the PHA backbone but no terminal thiol groups) is shown in FIG. 3. It will be appreciated that similar reactions may occur between the thiol group(s) depicted in the other example functionalized PHA materials depicted in FIG. 2A (or the materials depicted in FIGS. 2B-2D) to form disulfide linkage(s).

Figure 4:
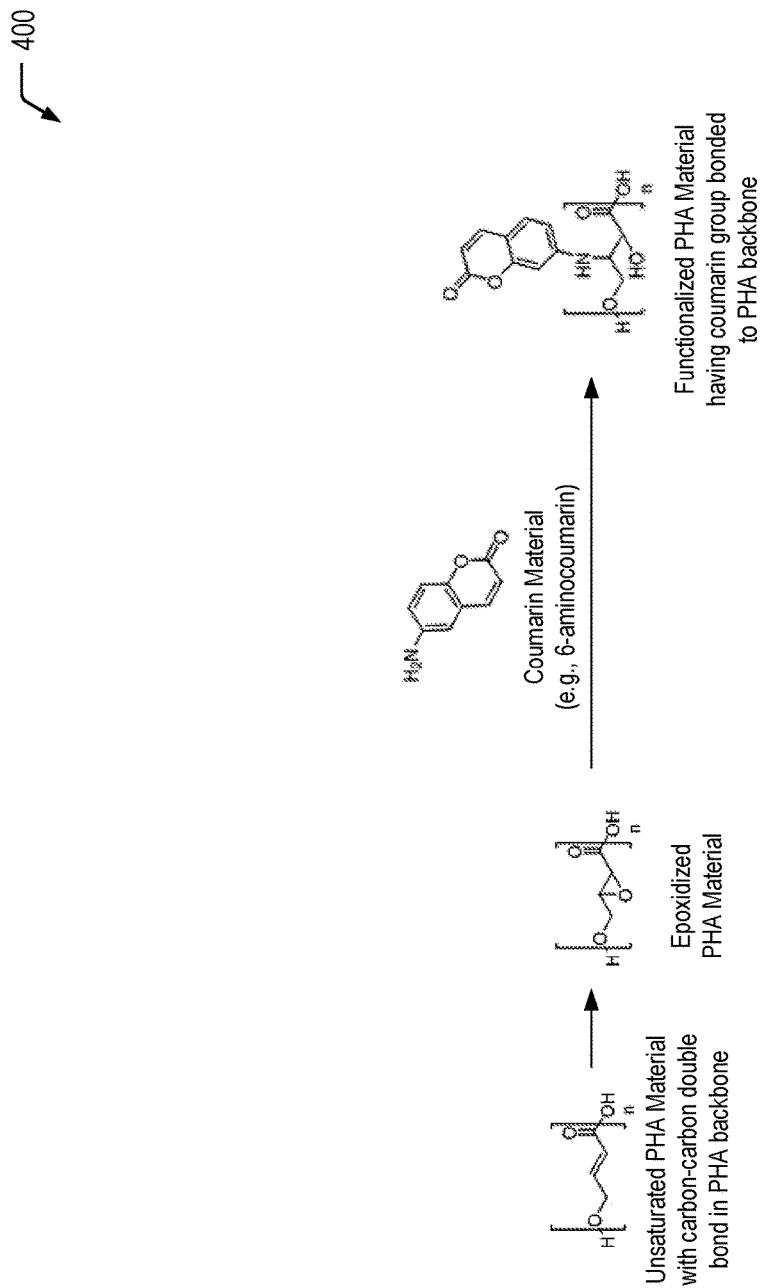
FIG. 4 is a chemical reaction diagram illustrating a process of utilizing the unsaturated PHA material depicted in FIG. 1 to form a functionalized PHA material containing a coumarin group bonded to a PHA backbone, according to one embodiment.

Referring to FIG. 4, a chemical reaction diagram 400 illustrates an example of a process of utilizing the unsaturated PHA material having the carbon-carbon double bond in the PHA backbone that is depicted in FIG. 1 to form a functionalized PHA material containing a coumarin group bonded to the PHA backbone, according to one embodiment. As illustrated and further described herein with respect to FIG. 5, a reversibly cross-linked PHA material may be formed via a coumarin photodimerization reaction.

The first chemical reaction depicted in FIG. 4 illustrates that the carbon-carbon double bond in the PHA backbone of the unsaturated PHA material of FIG. 1 may be utilized to form an epoxidized PHA material having an epoxide group in the PHA backbone. The second chemical reaction depicted in FIG. 4 illustrates that the epoxidized PHA material may be chemically reacted with a coumarin material to form a functionalized PHA material having a coumarin group bonded to the PHA backbone. In the particular embodiment depicted in FIG. 4, the coumarin material includes 6-aminocoumarin. In other cases, alternative and/or additional coumarin materials may be utilized. As illustrated and described further herein with respect to FIG. 5, a coumarin photodimerization reaction may be utilized to form a reversibly cross-linked PHA material.

As a prophetic example, with regard to the aminocoumarin epoxide ring-opening, possible catalysts may include calcium triflate catalyst in acetonitrile (or DMF, chloroform, etc.) or zinc (II) perchlorate hexahydrate (2 mol percent) neat, room temperature or 80° C. (although this may be difficult to run neat with polymer, would need to run at a temperature above melting point for polymer). Alternatively, the reaction may run neat with heat, similar to curing an epoxy/amine resin system.

While not shown in the example of FIG. 4, it may be possible to have the aminocoumarin be bonded to the other carbon of the epoxide ring and for the hydroxyl group to be located one carbon further away from the terminal carboxylic acid group. Also, it may be possible that the aminocoumarin reacts with the terminal hydroxyl group.

Thus, FIG. 4 illustrates an example of a process of utilizing the unsaturated PHA material depicted in FIG. 1 to form a functionalized PHA material containing a coumarin group bonded to a PHA backbone. As further described herein, the coumarin group depicted in FIG. 4 may be utilized to form a PHA material that is reversibly cross-linked via a coumarin photodimerization reaction.

Figure 5:
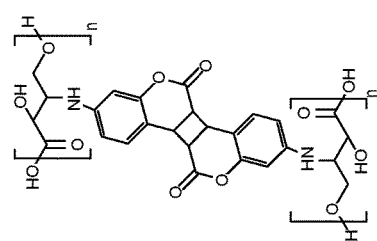
FIG. 5 is a chemical reaction diagram illustrating a process of utilizing the functionalized PHA material depicted in FIG. 4 to form a reversibly cross-linked PHA material, according to one embodiment.
Figure 5:
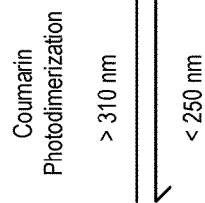
Figure 5:
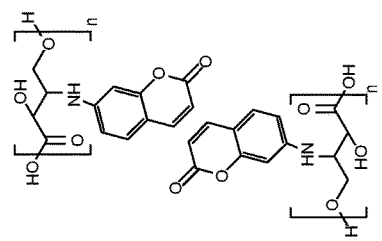

Referring to FIG. 5, a chemical reaction diagram 500 illustrates an example of a process of utilizing the functionalized PHA material depicted in FIG. 4 to form a reversibly cross-linked PHA material via a coumarin photodimerization reaction. For example, exposure of the functionalized PHA material depicted in FIG. 4 to UV light having a wavelength that is greater than 310 nm may result in the cross-linked PHA material depicted on the right side of FIG. 5. Exposure of the functionalized PHA material depicted in FIG. 4 to UV light having a wavelength that is less than 250 nm may reverse the chemical reaction.

Figure 6:
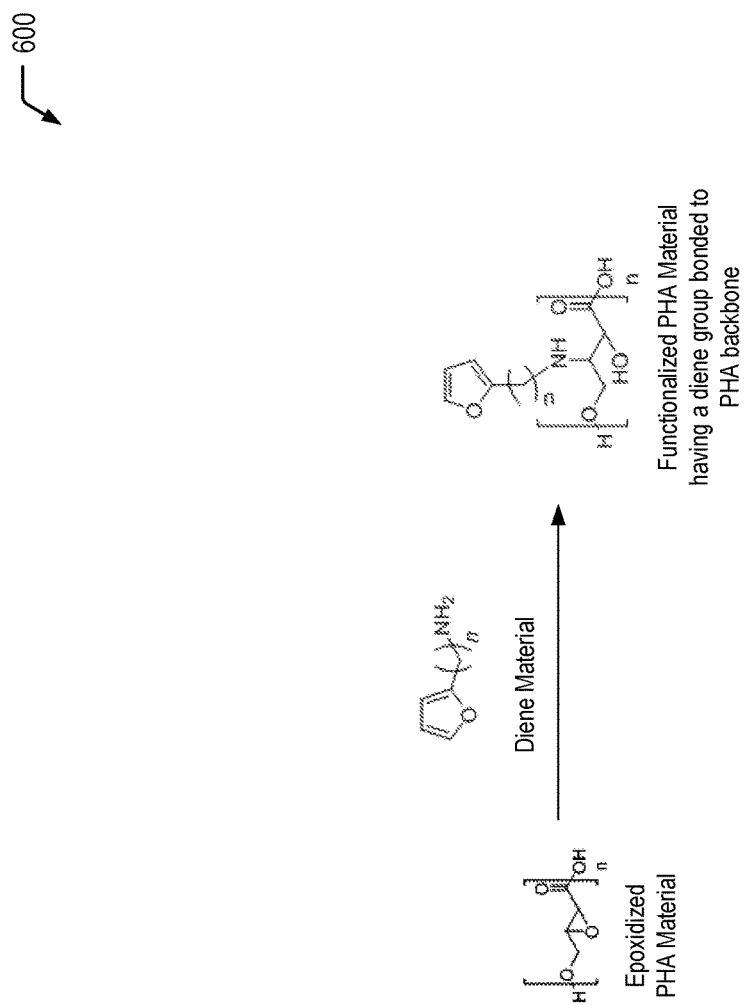
FIG. 6 is a chemical reaction diagram illustrating a process of utilizing the unsaturated PHA material depicted in FIG. 1 to form a functionalized PHA material containing a diene group bonded to a PHA backbone, according to one embodiment.

Referring to FIG. 6, a chemical reaction diagram 600 illustrates an example of a process of utilizing the unsaturated PHA material having the carbon-carbon double bond in the PHA backbone that is depicted in FIG. 1 to form a functionalized PHA material containing a diene group bonded to a PHA backbone, according to one embodiment. As illustrated and further described herein with respect to FIG. 8, a Diels-Alder reaction between the diene group of the functionalized PHA material of FIG. 6 and the dienophile group of the functionalized PHA material of FIG. 7 may enable the formation of a reversibly cross-linked PHA material.

FIG. 6 illustrates that the epoxidized PHA material may be chemically reacted with a diene material to form a functionalized PHA material having a diene group bonded to the PHA backbone. While not shown in FIG. 6, the epoxidized PHA material may be formed via an epoxidation reaction of the PHA backbone that is depicted in FIG. 1, as previously described herein. In the particular embodiment depicted in FIG. 6, the diene material includes an amine-functionalized furan. In other cases, alternative and/or additional diene materials may be utilized. As illustrated and described further herein with respect to FIG. 8, a reversibly cross-linked PHA material may be formed via a Diels-Alder reaction between the diene group of the functionalized PHA material of FIG. 6 and the dienophile group of the functionalized PHA material of FIG. 7.

Thus, FIG. 6 illustrates an example of a process of utilizing the unsaturated PHA material depicted in FIG. 1 to form a functionalized PHA material containing a diene group bonded to a PHA backbone. As further described herein, a Diels-Alder reaction between the diene group depicted in FIG. 6 and a dienophile group (e.g., the dienophile group depicted in FIG. 7) may result in the formation in a reversibly cross-linked PHA material.

Figure 7:
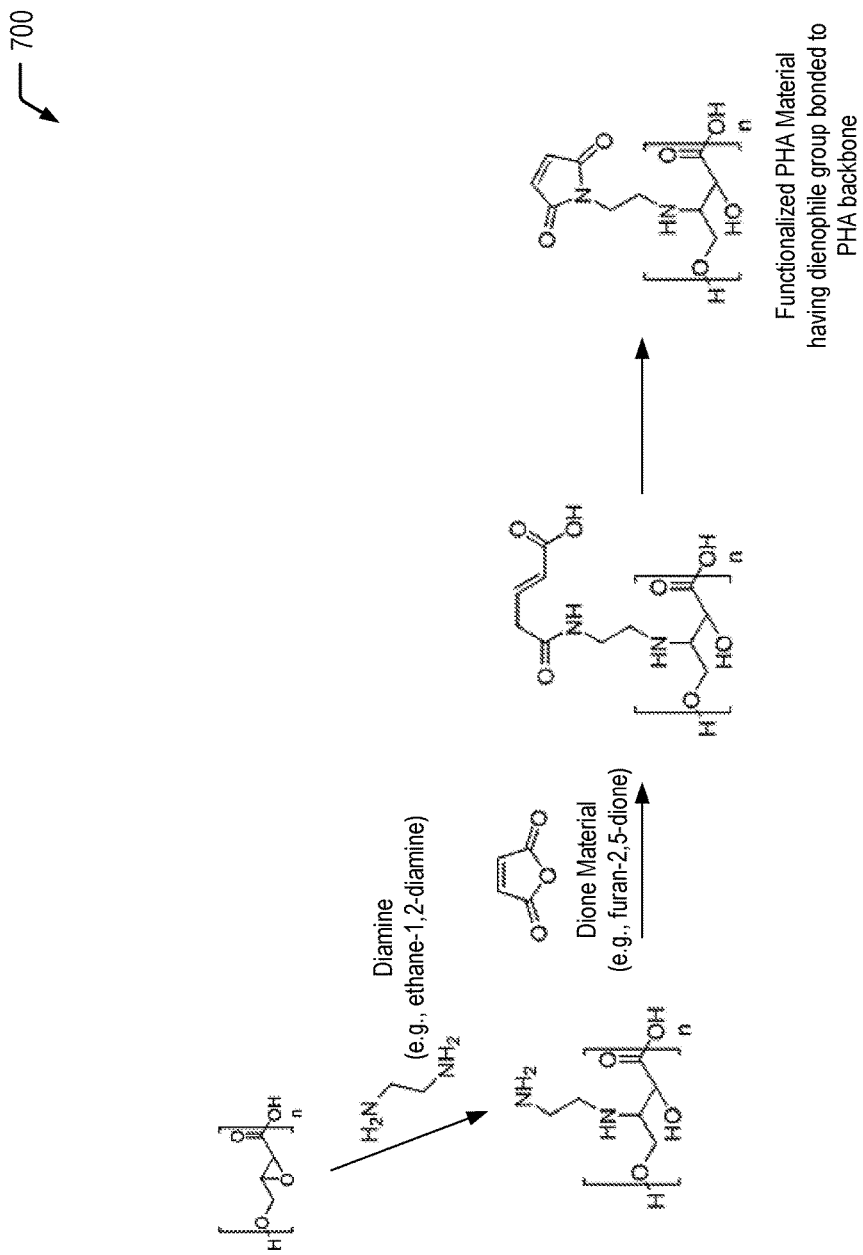
FIG. 7 is a chemical reaction diagram illustrating a process of utilizing the unsaturated PHA material depicted in FIG. 1 to form a functionalized PHA material containing a dienophile group bonded to a PHA backbone, according to one embodiment.

Referring to FIG. 7, a chemical reaction diagram 700 illustrates an example of a process of utilizing the unsaturated PHA material having the carbon-carbon double bond in the PHA backbone that is depicted in FIG. 1 to form a functionalized PHA material containing a dienophile group bonded to a PHA backbone, according to one embodiment. As illustrated and further described herein with respect to FIG. 8, a Diels-Alder reaction between the dienophile group of the functionalized PHA material of FIG. 7 and the diene group of the functionalized PHA material of FIG. 6 may enable the formation of a reversibly cross-linked PHA material.

The first chemical reaction depicted in FIG. 7 illustrates that an epoxidized PHA material may be chemically reacted with a diamine to form an intermediate material that includes a pendant amine group. While not shown in FIG. 7, the epoxidized PHA material may be formed via an epoxidation reaction of the PHA backbone that is depicted in FIG. 1, as previously described herein. In the particular embodiment depicted in FIG. 7, the diamine includes ethane-1,2-diamine. In other cases, alternative and/or additional diamine materials may be utilized.

As a prophetic example, with regard to the diaminoethane reaction of FIG. 7, one equivalent of the epoxidized PHA material may be dissolved in more than 4 equivalents of a diamine (e.g., ethane-1,2-diamine) and stirred overnight at 100° C. in a sealed tube. Excess diamine may be removed under reduced pressure to obtain crude product. In some cases, common organic solvents that dissolve the polymer may be utilized. A similar catalyst system as described with respect to the aminocoumarin reaction of FIG. 5 may be utilized. With regard to the diamine, other alkyl chains may be used, such as propyl, butyl, pentyl, or hexyl chains, among other alternatives. A mono-protected amine may be used as well, then subsequently deprotected. An example of a protecting group may include a tBoc (tert-butyloxycarbonyl) group.

The second chemical reaction depicted in FIG. 7 illustrates that the intermediate material may be chemically reacted with a dione material to form a second intermediate material having a pendant dione group. In the particular embodiment depicted in FIG. 7, the dione material includes furan-2,5-dione. In other cases, alternative and/or additional dione materials may be utilized. In a particular embodiment, the second chemical reaction may occur in the presence of a suitable solvent (e.g., chloroform, THF, DMF, etc.) at room temperature for about two hours.

The third chemical reaction depicted in FIG. 7 illustrates that the second intermediate material including the pendant dione group may be utilized to form a functionalized PHA material having a dienophile group bonded to the PHA backbone. In a particular embodiment, the third chemical reaction may proceed in the presence of p-TSA (p-toluenesulfonic acid), DMF, and toluene at a temperature of about 110° C.

Thus, FIG. 7 illustrates an example of a process of utilizing the unsaturated PHA material depicted in FIG. 1 to form a functionalized PHA material containing a dienophile group bonded to a PHA backbone. As illustrated and described further herein with respect to FIG. 8, a reversibly cross-linked PHA material may be formed via a Diels-Alder reaction between the dienophile group of the functionalized PHA material of FIG. 7 and the diene group of the functionalized PHA material of FIG. 6.

Figure 8:
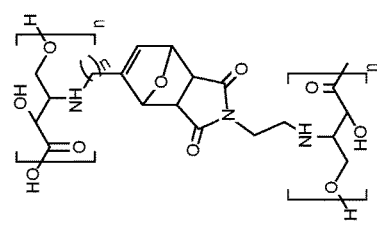
FIG. 8 is a chemical reaction diagram illustrating a process of utilizing the functionalized PHA materials depicted in FIGS. 6 and 7 to form a reversibly cross-linked PHA material, according to one embodiment.
Figure 8:
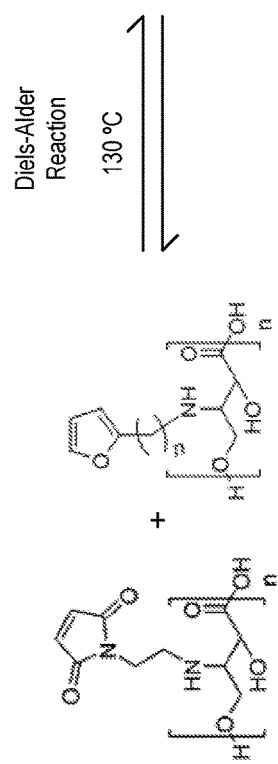

Referring to FIG. 8, a chemical reaction diagram 800 illustrates an example of a process of utilizing the functionalized PHA materials depicted in FIGS. 6 and 7 to form a reversibly cross-linked PHA material via a Diels-Alder reaction. FIG. 8 illustrates that, at a temperature that is greater than 130° C., the PHA backbone of the functionalized PHA material depicted in FIG. 6 may be coupled to the PHA backbone of the functionalized PHA material depicted in FIG. 7. At a temperature that is less than 130° C., the reaction may be reversed.

Figure 9:
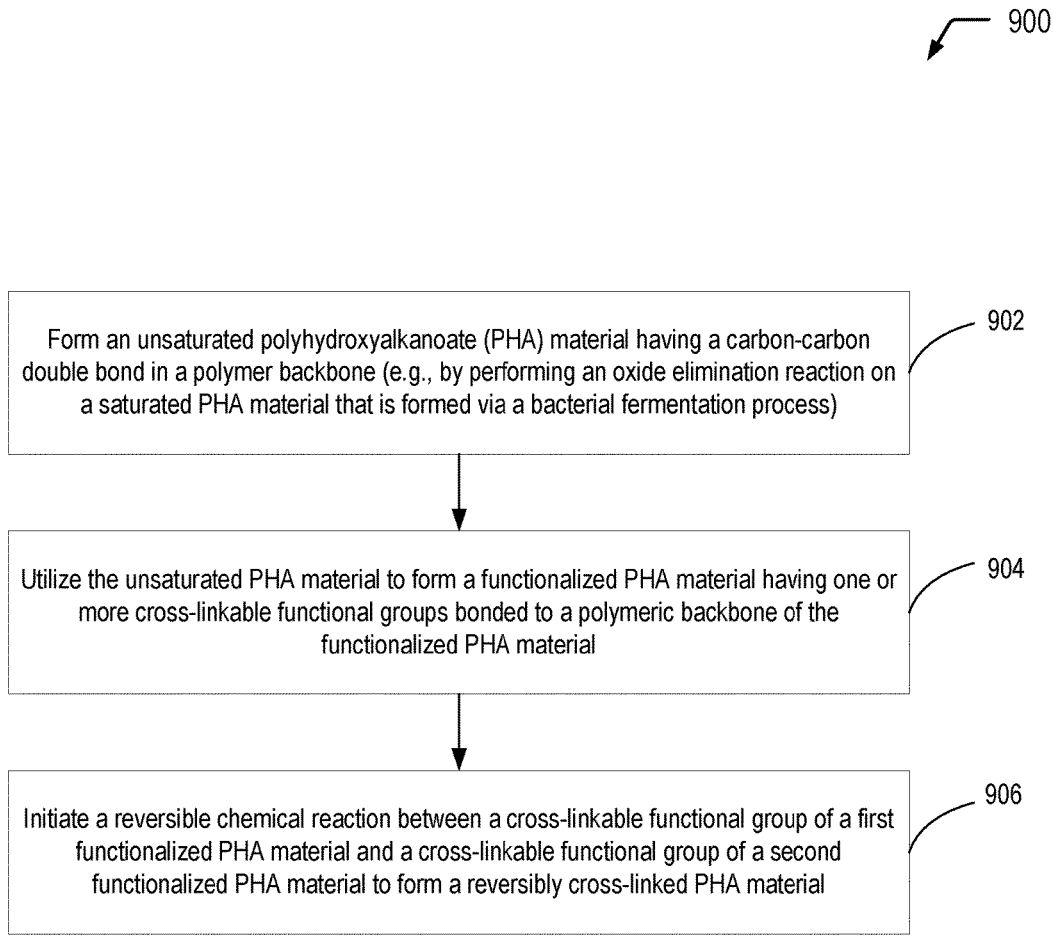
FIG. 9 is a flow diagram showing a particular embodiment of a process of utilizing an unsaturated PHA material having a carbon-carbon double bond in a polymer backbone to form a functionalized PHA material.

Referring to FIG. 9, a flow diagram illustrates a particular embodiment of a process 900 of utilizing an unsaturated PHA material having a carbon-carbon double bond in a polymer backbone to form a functionalized PHA material. In the particular embodiment depicted in FIG. 9, the process 900 also includes forming a reversibly cross-linked PHA material from the functionalized material. In the particular embodiment illustrated in FIG. 9, operations associated with an example process of forming a functionalized PHA material having cross-linkable functional group(s) are identified as operations 902-904, while operations associated with utilizing the functionalized PHA material to form a reversibly cross-linked PHA material are identified as operation 906. It will be appreciated that the operations shown in FIG. 9 are for illustrative purposes only and that the operations may be performed in alternative orders, at alternative times, by a single entity or by multiple entities, or a combination thereof. As an example, one entity may form the unsaturated PHA material having the carbon-carbon double bond in the PHA backbone (e.g., via a bacterial fermentation process and oxide elimination reaction), another entity may utilize the unsaturated PHA material to form the functionalized PHA material, while another entity may form the reversibly cross-linked PHA material.

The process 900 includes forming an unsaturated PHA material having a carbon-carbon double bond in a polymer backbone, at 902. For example, referring to FIG. 1, an oxide elimination reaction (e.g., a selenoxide elimination reaction) may be performed on the saturated PHA material (e.g., P4HB in the example of FIG. 1). In an alternative embodiment (not shown in FIG. 1), a sulfoxide elimination process may be utilized to form the PHA material having the carbon-carbon double bond in the polymer backbone.

The process 900 includes utilizing the unsaturated PHA material to form a functionalized PHA material having one or more cross-linkable functional groups bonded to a polymeric backbone of the functionalized PHA material, at 904. As an example, referring to FIGS. 2A-2D, the unsaturated PHA material depicted in FIG. 1 may be utilized to form a functionalized PHA material having cross-linkable thiol group(s) bonded to the PHA backbone. As another example, referring to FIG. 4, the unsaturated PHA material depicted in FIG. 1 may be utilized to form a functionalized PHA material having a photodimerizable coumarin group bonded to the PHA backbone. As a further example, referring to FIG. 6, the unsaturated PHA material depicted in FIG. 1 may be utilized to form a functionalized PHA material having a diene group bonded to the PHA backbone. As yet another example, referring to FIG. 7, the unsaturated PHA material depicted in FIG. 1 may be utilized to form a functionalized PHA material having a dienophile group bonded to the PHA backbone.

In the particular embodiment depicted in FIG. 9, the process 900 further includes initiating a reversible chemical reaction between cross-linkable functional groups of functionalized PHA materials to form a reversibly cross-linked PHA material, at 906. As an example, in the embodiment depicted in FIG. 3, the reversible chemical reaction includes a disulfide formation reaction between the thiol group(s) of the functionalized PHA material of FIG. 2A. As another example, in the embodiment depicted in FIG. 5, the reversible chemical reaction includes a coumarin photodimerization reaction. As yet another example, in the embodiment depicted in FIG. 8, the reversible chemical reaction includes a Diels-Alder reaction between the diene group of the functionalized PHA material of FIG. 6 and the dienophile group of the functionalized PHA material of FIG. 7.

Thus, FIG. 9 illustrates an example of a process of utilizing an unsaturated PHA material having a carbon-carbon double bond in a polymer backbone to form a functionalized PHA material having cross-linkable functional group(s). In the case of thiol functional group(s), a reversibly cross-linked PHA material may be formed via a disulfide formation reaction. In the case of a coumarin group, a reversibly cross-linked PHA material may be formed via a coumarin photodimerization reaction. In the case of diene/dienophile functional groups, a reversibly cross-linked PHA material may be formed via a Diels-Alder reaction. In contrast to PHA modification techniques where long alkyl chains extend from the polymer backbone, forming the carbon-carbon double bond in the PHA backbone prior to functionalization enables a variety of functional groups to be added closer to the PHA backbone. Bonding the functional groups closer to the PHA backbone results in a more rigid structure than PHA materials with long alkyl chains extending from the PHA backbone.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process of forming a functionalized polyhydroxyalkanoate (PHA) material, the process comprising:
    performing a selenoxide elimination reaction on a saturated PHA material to form an unsaturated PHA material having a carbon-carbon double bond in a polymer backbone; and
    utilizing the unsaturated PHA material to form a functionalized PHA material having one or more cross-linkable functional groups bonded to a polymer backbone of the functionalized PHA material, wherein the one or more cross-linkable functional groups include one or more thiol groups.

2. The process of claim 1, wherein the saturated PHA material is formed via a bacterial fermentation process.

3. The process of claim 1, wherein the saturated PHA material includes poly-4-hydroxybutyrate (P4HB).

4. A process of forming a functionalized polyhydroxyalkanoate (PHA) material, the process comprising:
    performing a sulfoxide elimination reaction on a saturated PHA material to form an unsaturated PHA material having a carbon-carbon double bond in a polymer backbone; and
    utilizing the unsaturated PHA material to form a functionalized PHA material having one or more cross-linkable functional groups bonded to a polymer backbone of the functionalized PHA material, wherein the one or more cross-linkable functional groups include one or more thiol groups.

5. The process of claim 4, wherein the saturated PHA material is formed via a bacterial fermentation process.

6. The process of claim 4, wherein the saturated PHA material includes poly-4-hydroxybutyrate (P4HB).

* * * * *